(12) United States Patent
Gilat

(10) Patent No.: US 6,395,722 B1
(45) Date of Patent: May 28, 2002

(54) FATTY ACID DERIVATIVES OF BILE ACIDS AND BILE ACID DERIVATIVES

(75) Inventor: Tuvia Gilat, Tel Aviv (IL)

(73) Assignee: Galmed International Limited, B'Kara (MT)

( * ) Notice: Subject to any disclaimer, the term of this patent is extended or adjusted under 35 U.S.C. 154(b) by 0 days.

(21) Appl. No.: 09/675,656

(22) Filed: Sep. 29, 2000

Related U.S. Application Data

(63) Continuation of application No. PCT/IL99/00173, filed on Mar. 25, 1999.

(30) Foreign Application Priority Data

Apr. 8, 1998 (IL) .................................................. 123998

(51) Int. Cl.⁷ .............................. A61K 31/56; C07J 9/00
(52) U.S. Cl. ........................ 514/182; 514/169; 552/553
(58) Field of Search ........................ 532/553; 514/169; 574/182

(56) References Cited

FOREIGN PATENT DOCUMENTS

DE          198 24 123      * 12/1999

* cited by examiner

*Primary Examiner*—Barbara P. Badio
(74) *Attorney, Agent, or Firm*—Jacobson Holman, PLLC

(57) ABSTRACT

The present invention relates to bile acid or bile salt fatty acid conjugates (hereinafter called "BAFAC), to their use in dissolving cholesterol gallstones in bile, preventing their occurrence or recurrence, to their use in reducing or preventing arteriosclerosis and to methods for the treatment of said diseases. The conjugates are of the formula W—X—G in which G is a bile acid or bile salt radical, W stands for one or two fatty acid radical(s) having 18–22 carbon atoms and X stands for a NH bond between said bile acid or bile salt radical and the fatty acid radical(s). The conjugation is advantageously performed at a position selected among the 3, 6, 7, 12 and 24 positions of the bile acid or bile salt nucleus.

19 Claims, 8 Drawing Sheets

1

2  n = 20
4  n = 18
6  n = 16

3  n = 20
5  n = 18
7  n = 16

16

17

18

1

19

20

Chain length of conjugated fatty acids

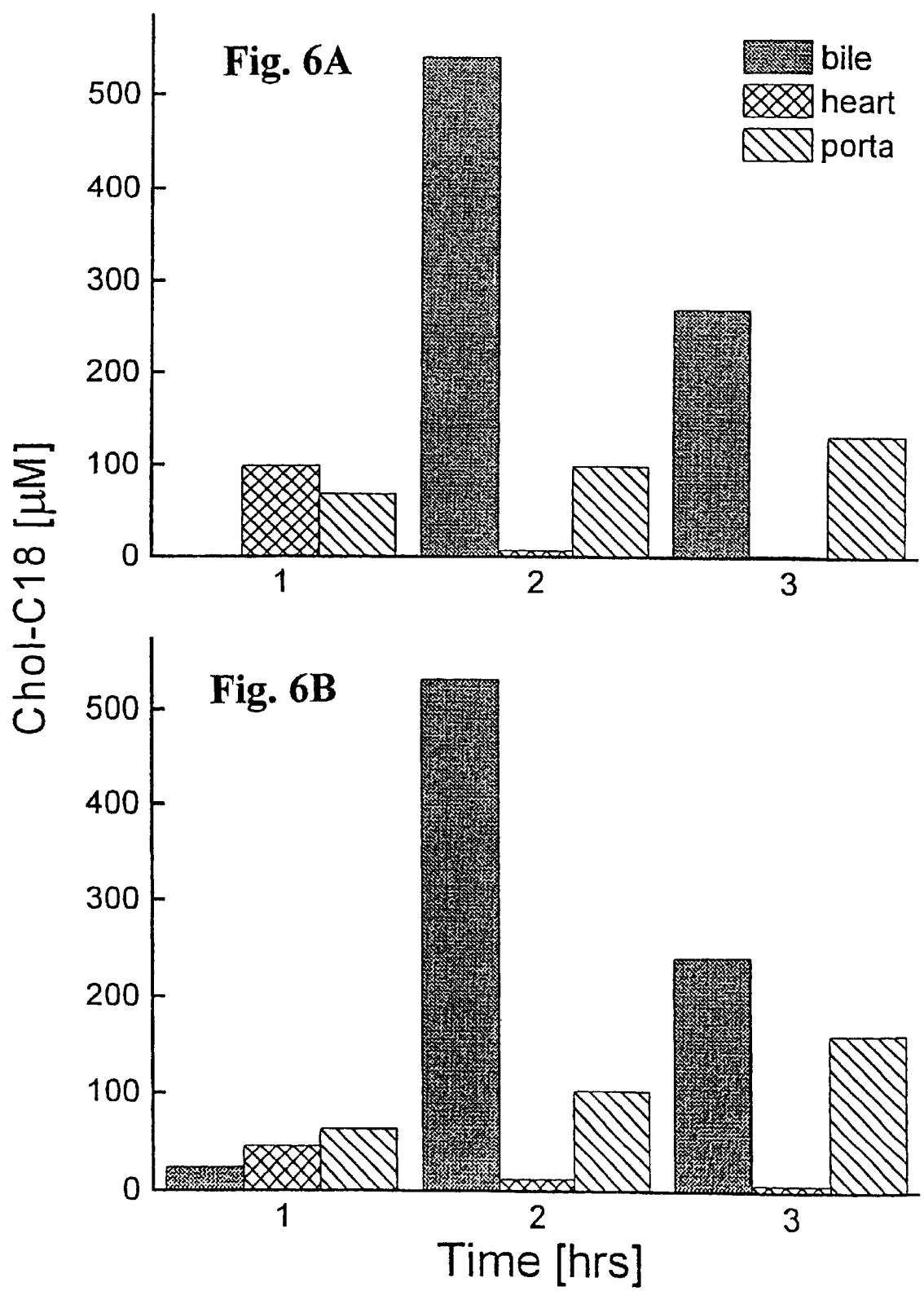

FATTY ACID DERIVATIVES OF BILE ACIDS AND BILE ACID DERIVATIVES

FATTY ACID DERIVATIVES OF BILE ACIDS AND BILE ACID DERIVATIVES

Related Application

This application is a continuation of PCT/IL99/00173 filed Mar. 25, 1999.

The present invention relates to bile acid or bile salt fatty acid conjugates (hereinafter called "BAFAC"), to their use in dissolving cholesterol gallstones in bile, preventing their occurrence or recurrence, to their use in reducing or preventing arteriosclerosis and to methods for the treatment of said diseases.

It should be noticed that the terms bile acids and bile salts are similar and are used interchangeably.

Gallstones are found in about 15% of people in most industrialized countries. Most gallstones are cholesterol gallstones, i.e. cholesterol being their main component. Thus, cholesterol gallstones represent a major health problem. Bile is often supersaturated with cholesterol which tends to crystallize. The prevention of cholesterol crystallization in bile will prevent the formation of cholesterol gallstones or their recurrence after procedures such as lithotripsy, dissolution, or stone extraction. The residence time of newly secreted bile in the gallbladder is short—less than 12–24 hours. The prevention of cholesterol crystallization in bile during such a period could prevent gallstone formation.

It has been proven that cholesterol gallstones can be dissolved medically and their recurrence prevented using certain bile salts such as chenodeoxycholic or ursodeoxycholic acid. Bile salt therapy is, however, of low efficacy, is very time consuming and has been largely abandoned. More effective therapies are thus required.

Recent work has demonstrated the major role played by phospholipids in cholesterol solubilization in bile. (T. Gilat et. al. Biochimica et Biophysica Acta 1286, (1996), 95–115; Y. Ringel et al. Biochimica et Biophysica Acta 1390, (1998), 293–300,); and J. Heptalogy, 28, (1998), 1008–1014.) Phospholipids are a major or sole component of cholesterol solubilizing lipid aggregates in bile. It has been demonstrated that the stepwise addition of phospholipids to bile will progressively prolong the nucleation time of the cholesterol in bile. (Z. Halpern et. al. Gut 34 (1993) 110–115).

Major differences between certain phospholipid molecular species in their cholesterol crystallization inhibiting potency in human or model biles have been demonstrated. Phospholipids differ from one another mainly in the fatty acids present in the stereo-specific number sn-1 and/or sn-2 positions and in their head groups. It has been demonstrated that major prolongations in the nucleation time and major reductions in the cholesterol crystal growth rate and in the total cholesterol crystal mass are achieved with changes in phospholipid molecular species without changing the absolute or relative amounts of phospholipids. Cholesterol crystallization was markedly delayed when the sn-2 fatty acid was saturated, when the head group was serine instead of choline, etc. (Y. Ringel et. al. above).

It has also been shown that various phospholipid components by themselves (without the whole phospholipid molecule), e.g. saturated fatty acids such as palmitic acid or stearic acid; or phosphatidyl glycerol have strong cholesterol crystallization inhibiting activity.

Thus, enriching human bile with phospholipids in general, or specific phospholipids or their components, such as fatty acids would markedly retard cholesterol crystallization in bile and achieve the desired result.

The problem was how to enrich human bile in vivo with phospholipids or their components. While bile salts are fed to humans they are very efficiently absorbed, taken up by the liver and excreted into bile. This also applies to synthetic bile salt analogues. There are specific and very efficient transport mechanisms in the body for these purposes. Thus, when ursodeoxycholic acid (which is normally present in human bile in minute amounts) is fed regularly it is absorbed and secreted into bile and eventually constitutes 30–50% of biliary bile acids. However, as indicated above bile salt therapy for the dissolution of cholesterol gallstones is not satisfactory.

Phospholipids and their components are well absorbed and taken up by the liver. Phospholipid secretion into bile is, however, tightly regulated by the liver and only limited amounts and species of phospholipids are secreted into bile in association with the secretion of bile salts and cholesterol. There is at present no efficient method to modulate, quantitatively or qualitatively, human biliary phospholipid compositions to any considerable degree. When dietary phospholipids reach the liver they may be metabolized, secreted into the blood or stored in the liver. Only small amounts and predetermined species are secreted into bile with minimal possibilities for modulation.

It has therefore been desirable to find a satisfactory method for the transport of phospholipids or one of their components into bile which would improve the solubilization of biliary cholesterol and prevent the formation of cholesterol gallstones or dissolve existing gallstones.

From Israel Patent specification No. 95668 and corresponding U.S. Specifications there are known bile acid derivatives of general formula I:

W—X—G in which G is a bile acid radical, W is an active compound moiety of a medicament and X is either a direct bond or a bonding member between said bile acid radical and the active compound. In said specifications a long list of substituents is given but it does not mention specifically W as standing for a fatty acid radical, neither for a saturated one nor for an unsaturated one, i.e. said specifications do not mention anything about BAFAC.

Moreover, among all the objects of said compounds their cannot be found even a hint that any of said compounds may be utilized to enhance the solubilization of biliary cholesterol, to prevent the formation of cholesterol gallstones, to dissolve existing cholesterol gallstones, to reduce or prevent arteriosclerosis.

It has now been found that bile acids or salts conjugated with fatty acids (saturated or unsaturated) via a connecting bond —NH— (BAFAC) can serve as vehicles to transport the fatty acids into the bile using the very efficient enterohepatic circulation of bile acids and salts.

An ester bond between the fatty acid(s) and the bile acid is unsuitable as it would be broken down by digestive juices and intestinal bacteria during absorption and enterohepatic circulation. Only a fraction of the intact BAFAC will remain in the bile.

It has also been shown that BAFAC are absorbed from the intestine, taken up by the liver and secreted into bile. Said BAFAC improved cholesterol solubilization in bile and markedly retarded its crystallization. Said BAFAC are therefore useful agents for the prevention of the formation or recurrence of cholesterol gallstones and for the dissolution of cholesterol gallstones.

The administration of BAFAC has also an inhibiting effect on cholesterol crystallization in the vascular tree. In the physiologic situation ingested bile acids or salts are absorbed in the intestine, transported via the portal vein to the liver and excreted via the bile into the intestine. They thus recirculate in the entero-hepatic circulation, with only small amounts reaching the systemic circulation (the vascular tree). The BAFAC behave more like lipids, which after intestinal absorption are transported via the lymph to the systemic circulation. The BAFAC were shown to be transported both via the lymph and via the portal vein. By both routes they are taken up by the liver and secreted into the bile. At each entero-hepatic circulation they are excreted into the intestine, are again partly reabsorbed via the lymph and recirculated into the vascular tree prior to liver uptake. As there are daily 10–12 cycles of entero-hepatic circulation the net effect will be recirculation of the BAFAC in the vascular tree.

Administration of BAFAC orally in divided doses in the course of the day will enhance this effect. The inhibiting effect of BAFAC on cholesterol crystallization and their effectiveness in dissolving existing cholesterol crystals has been proven. Thus, also their value in reducing and/or preventing cholesterol crystallization in the vascular tree, i.e. in arteriosclerosis.

The present invention thus consists in bile acid or bile salt fatty acid conjugates of general formula II:

in which G has the same meaning as in formula I, which, if desired, is conjugated in position 24 with a suitable amino acid, W stands for one or two fatty acid radicals having 18–22 carbon atoms and X stands for a NH bond between said bile acid or bile salt radical and the fatty acid radical(s).

As suitable bile acids they may be mentioned, e.g. cholic acid, chenodeoxycholic acid, ursodeoxycholic acid and deoxycholic acid. The bile acids utilized may be unconjugated or, as in bile, be conjugated with glycine, taurine or another suitable amino acid. These possibilities are within the definition of a bile acid and thus within the scope of the present invention. The conjugation with the fatty acid radical is mostly performed at position 3 of the nucleus depending on the bile acid being used. It is also possible to perform the conjugation with the fatty acid radical at different positions, e.g. 6, 7, 12 and 24. When the bile acid is conjugated with glycine or taurine the conjugation with the fatty acid radical cannot be performed in position 24. The conjugation between the fatty acid radical and the bile acid can be in the α or the β configuration.

Preferred fatty acids are saturated ones which have suitably 18–22 carbon atoms. Preferred saturated fatty acids are behenylic acid, arachidylic acid and stearic acid.

When W stands for two fatty acids they are suitably conjugated at positions 3 and 7.

The present invention also consists in a pharmaceutical composition enabling the dissolution of cholesterol gallstones in bile and preventing the formation thereof; and enabling the prevention and/or reduction of arteriosclerosis, comprising as active ingredient a bile acid fatty acid derivative of general formula II.

Said composition may have the form of a tablet, a capsule, a solution, an emulsion, etc.

Said composition may comprise additional compounds such as carriers, solvents, emulgators, enhancers of absorption, inhibitors of cholesterol synthesis or secretion into the bile, etc. Said composition should advantageously comprise 0.1–1.5 g of the active ingredient.

The composition is suitably ingested once daily preferably at bedtime. It may also be ingested in divided doses during the day.

The present invention also consists in the use of a bile acid fatty acid derivative of general formula II or of a pharmaceutical composition comprising same for the dissolution of cholesterol gallstones in bile and for the prevention of the formation thereof.

The present invention also consists in the use of a bile acid fatty acid derivative of general formula II or of a pharmaceutical composition comprising same for the prevention and/or reduction of arteriosclerosis.

The present invention also consists in a method for the dissolution of cholesterol gallstones in bile and for the prevention of the formation thereof by administering a bile acid fatty acid derivative of general formula II or a pharmaceutical composition comprising same.

The present invention also consists in a method for the prevention and/or reduction of arteriosclerosis by administering a bile acid fatty acid derivative of general formula II or a pharmaceutical composition comprising same.

The present invention will now be illustrated with reference to the accompanying Examples and drawings without being limited by them.

BRIEF DESCRIPTION OF THE DRAWINGS

FIGS. 6A and 6B show stearoyl (C-18) cholate levels in hamsters 1, 2 and 3 hours after ingestion of 30 mg. Concentrations in heart blood, portal blood and gallbladder bile.

EXAMPLE I

3β-Behenylamido-7α,12α-dihydroxy-5β-cholan-24-oic acid (FIGS. 1A–3)

Figure 1A:
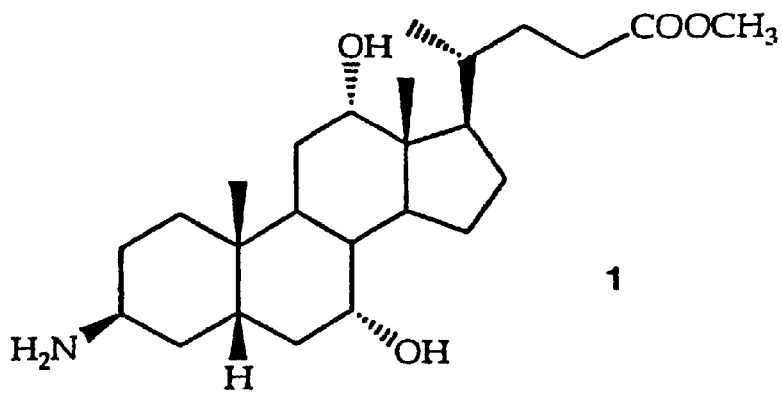
FIG. 1A shows steps in the conjugation of cholic acid (at C-3) with: benhenylic acid (C-22), arachidic acid (C-20) and stearic acid (C-18).
Figure 1A:
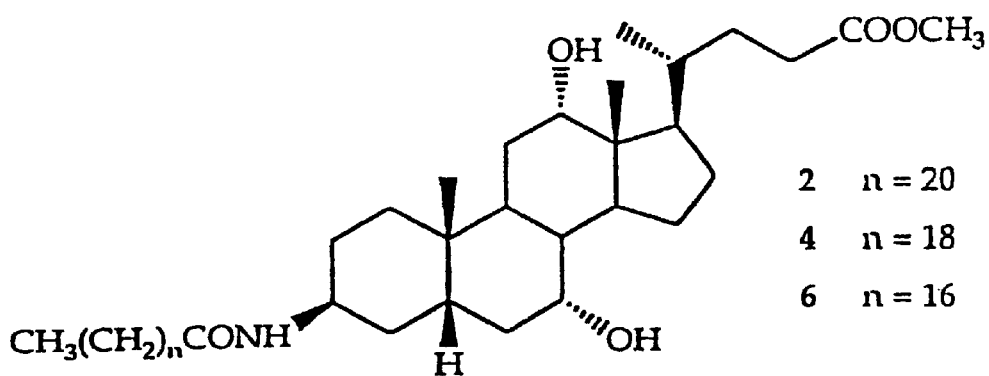
Figure 1A:
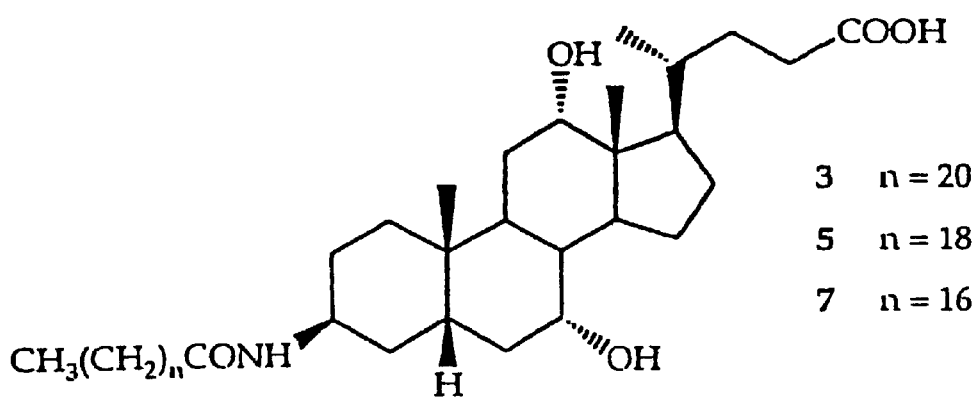
Figure 1B:
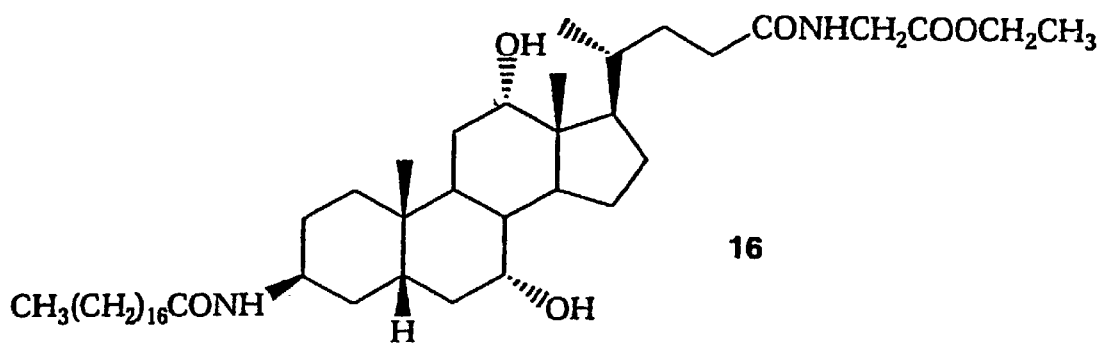
FIG. 1B shows stages in the synthesis of glycine conjugated stearoyl-cholate.
Figure 1B:
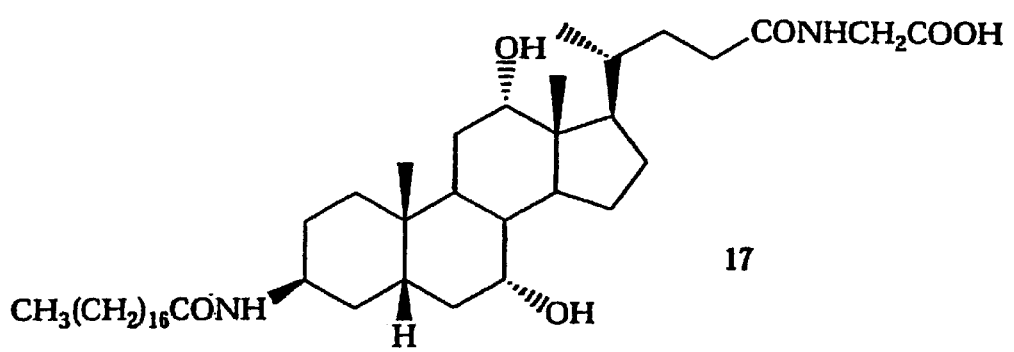
Figure 1B:
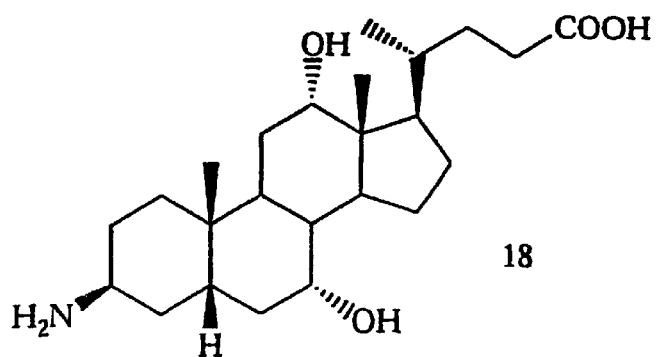
Figure 1C:
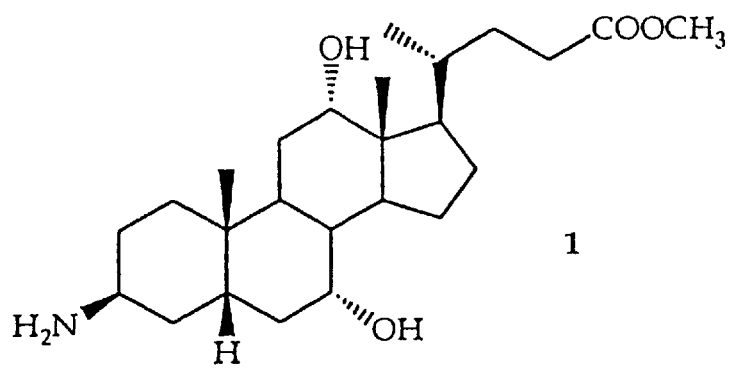
FIG. 1C shows conjugation of oleoyl-cholate.
Figure 1C:
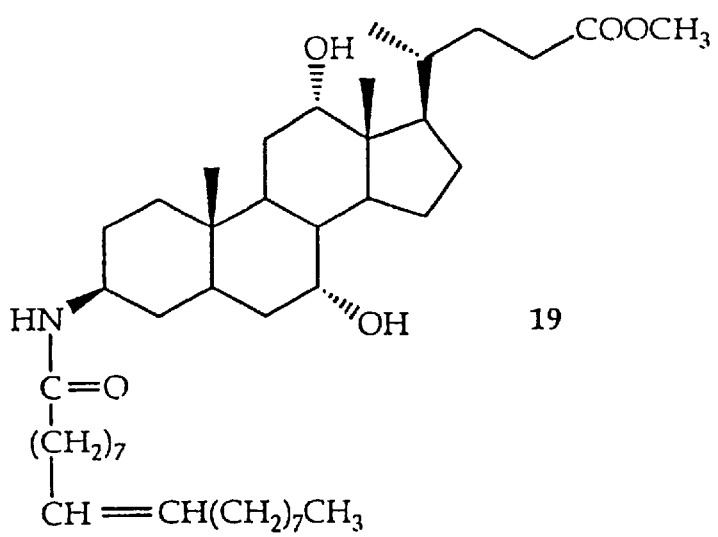
Figure 1C:
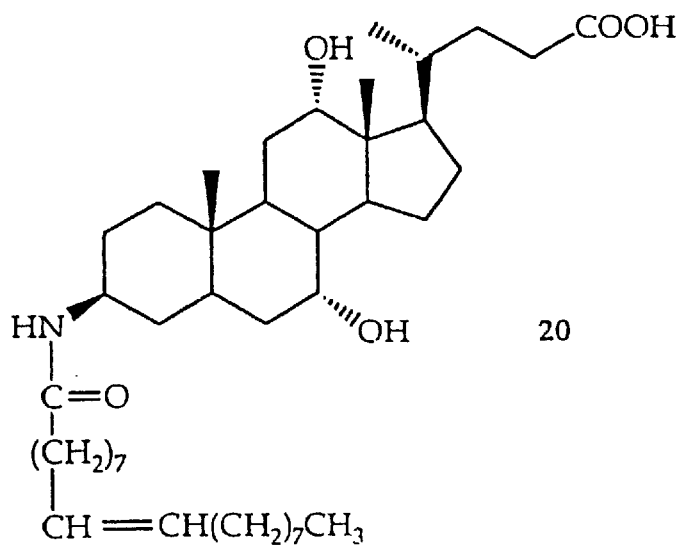
Figure 1D:
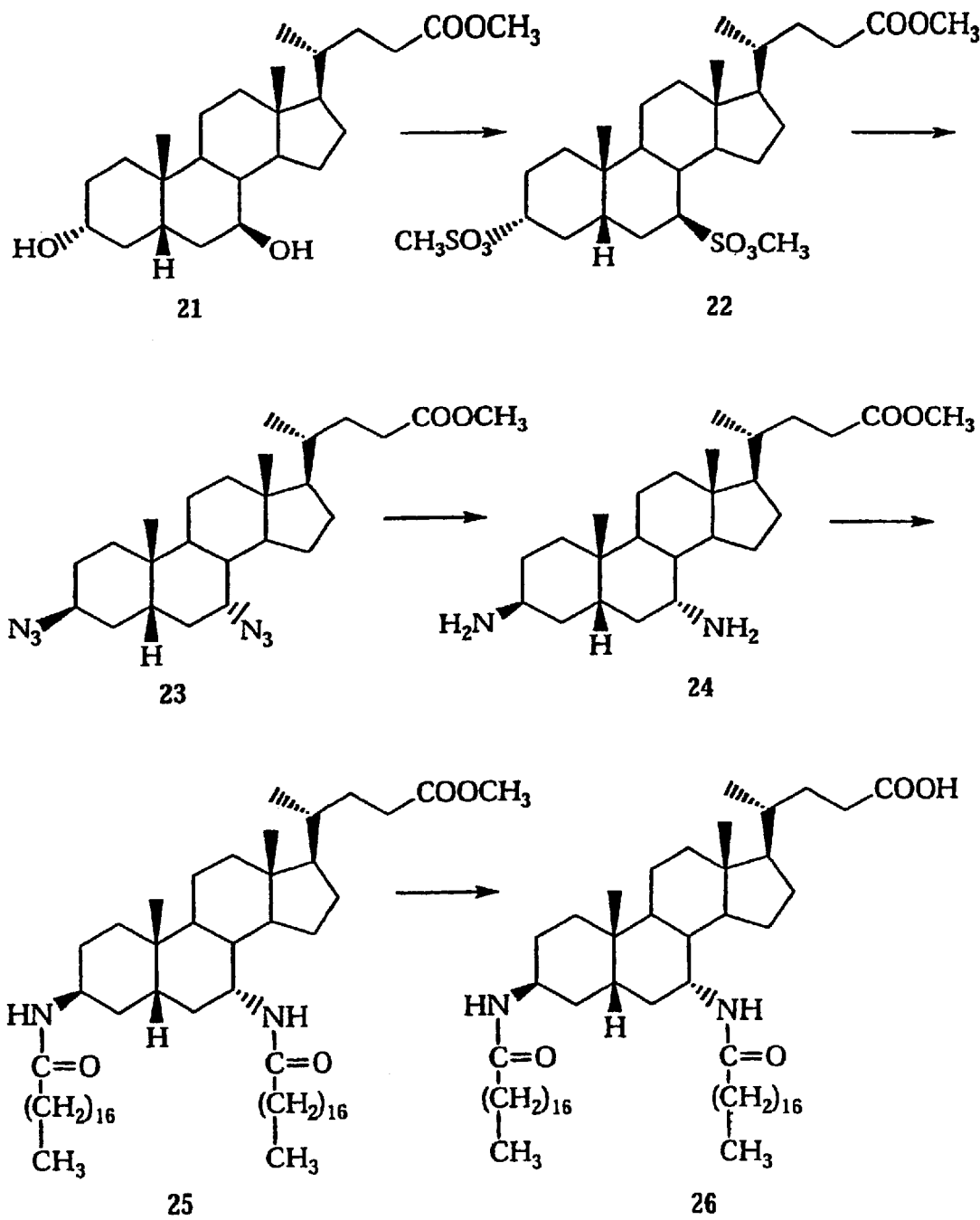
FIG. 1D shows conjugation of ursodeoxycholic acid with two molecules of stearic acid at positions C-3 and C-7 of the bile acid nucleus.
Figure 2:
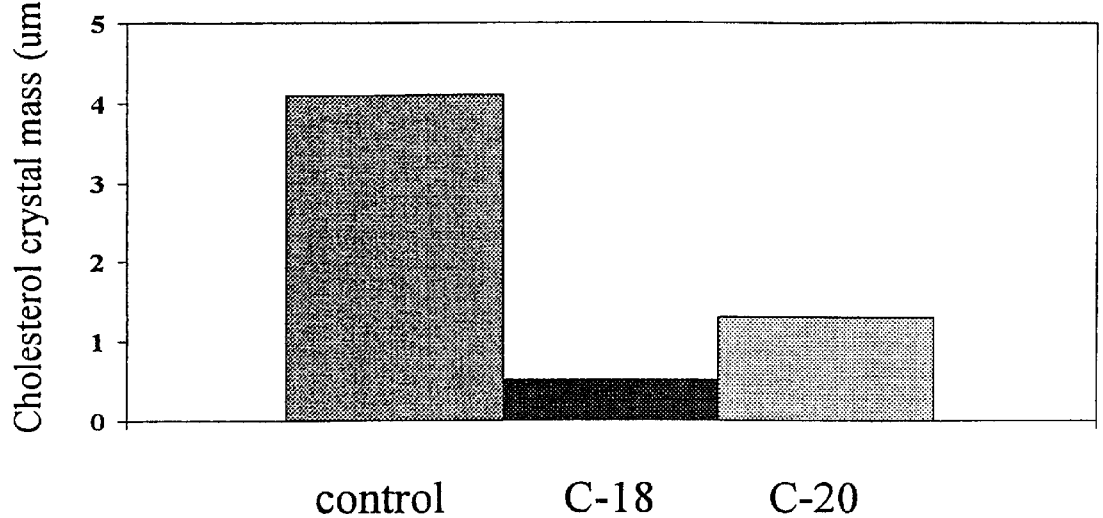
FIG. 2 shows the cholesterol crystal mass. Model bile solution. Effects of BAFACs comprising stearic (C-18) and arachidic (C-20) acids conjugated with cholic acid (at C-3). The test compounds replaced 20 mole % of the NaTC in the control solution.

(a) 1.15 g of 3β-amino-7α,12α-dihydroxy-5β-cholan-24 oic methylester (FIGS. 1A–I) [Fr Patent 1017756 Dec. 18 1952, Chem. Abstr. 52:1293c] were dissolved in 30 ml dry dimethyl formamide and treated with 15 ml triethyl amine under stirring. 1.13 g of behenoyl chloride in 10 ml dimethyl formamide were added dropwise to the resulting solution, and the stirring was continued overnight. The reaction mixture was poured into water extracted with methylene chloride, the organic fraction was then dried over sodium sulfate, evaporated to dryness and chromatographed over silica gel with a mixture of ethyl acetate and hexane (6:4 and 8:2), to give 0.8 g of 3β-behenylamido-7α,12α-dihydroxy-5β-cholan-24-oic of the methyl ester (FIGS. 1A–2).

$^1$H-NMR (CDCl$_3$) δ, ppm: 0.69 (s, CH$_3$-18), 0.88 (t, J=1 Hz, CH$_3$-23), 0.95 (s.CH$_3$-19), 0.99 (d, J=3 Hz, CH$_3$-21), 1.25, 1.14[s, CH$_2$)$_{20}$], 2.14 (t, J=5 Hz, CH$_3$-behenyl), 3.67 (s-COOCH$_3$), 3.91 (d, J=1.5 Hz, CH-7), 3.96 (s, J=4 Hz, CH-12), 3.99 (m, CH-3), 5.60 (d, J==4.5 Hz, —CH$_2$CO—).

(b) The above methyl ester, 0.45 g, was dissolved in 20 ml methanol, treated with 2 ml 1N sodium hydroxide and left for 24 h at room temperature. The methanol was then distilled off, 10 ml water were added and the reaction mixture was extracted with ethyl acetate. The water fraction was then acidified with diluted acid chloride, resulting in a white precipitate which was washed with water, to give 0.41 g of the pure 3β-behenylamido-7α,12α-dihydroxy-5β-cholan-24-oic acid (FIGS. 1A–3).

EXAMPLE II

3β-arachidylamido-7α,12α-dihydroxy-5β-cholan-24-oic acid (FIGS. 1A–5)

(a) 1.0 g of 3β-amino-7α,12α-dihydroxy-5β-cholan-24-oic methylester (FIGS. 1A–1) [see Example I] were dissolved in 30 ml dry dimethylformamide and treated with 15 ml triethyl amine under stirring. 1.0 g of arachidoyl chloride in 10 ml dimethylformamide were added dropwise to the resulting solution, and the stirring was continued overnight. The reaction mixture was poured into water, extracted with methylene chloride, the organic fraction was then dried over sodium sulfate, evaporated to dryness and chromatographed over silica gel with a mixture of ethyl acetate and hexane (6:4 and 8:2), to give 0.6 g 3β-arachidylamido-7α,12α-dihydroxy-5β-cholan-24-oic methylester (FIGS. 1A–4).

$^1$H-NMR (CDCl$_3$) δ, ppm: 0.70 (s, CH$_3$-18), 0.88 (t, J=6 Hz, CH$_3$-23), 0.95 (s, CH$_3$-19), 0.99 (d, J=3.0 Hz, CH$_3$-21) 1.25, 1.14 [(s, CH$_2$)$_{18}$], 2.14 (t, J=5 Hz, CH$_3$-arachidyl), 3.67 (s-COOCH$_3$), 3.91 (d, J=1.5 Hz, CH-7), 3.96 (t, J=4 Hz, CH-12), 4.4 (m, CH-3), 5.60 (d, J=4.5 Hz, —CH$_2$COHN).

(b) 0.5 g 3β-arachidylamido-7α,12α-dihydroxy-5β-cholan-24-oic methylester (FIGS. 1A–4) were dissolved in 20 ml methanol, treated with 2 ml 1N sodium hydroxide and left for 24 h at room temperature. The methanol was then distilled off, 10 ml water were added and the reaction mixture was extracted with ethyl acetate. The water fraction was then acidified with diluted hydrogen chloride, resulting in a white precipitate which was washed with water, to give 0.7 g of the pure 3β-arachidylamido-7α,12α-dihydroxy-5β-cholan-24-oic acid (FIGS. 1A–5).

EXAMPLE III

3β-stearylamido-7α,12α-dihydroxy-5β-cholan-24-oic acid (FIGS. 1A–7)

Method 1

(a) 1.15 g 3β-amino-7α,12α-dihydroxy-5β-cholan-024-oic methylester (FIGS. 1A–1) [see Example I] were dissolved in 30 ml dry dimethylformamide and treated with 15 ml triethyl amine under stirring. 1.13 g of stearoyl chloride in 10 ml dimethyl formamide were added dropwise to the resulting solution, and the stirring was continued overnight. The reaction mixture was poured into water extracted with methylene chloride, the organic fraction was then dried over sodium sulfate, evaporated to dryness and chromatographed over silica gel with a mixture of ethyl acetate and hexane (6:4 and 8:2), to give 0.68 g 3β-stearylamido-7α,12α-dihydroxy-5β-cholan-24 oic methylester (FIGS. 1A–6).

$^1$H-NMR (CDCl$_3$) δ, ppm: 0.69 (s, CH$_3$-18), 0.88 (t, J=1 Hz, CH$_3$-23), 0.95 (s, CH$_3$-19), 0.99 (t, J=3.0 Hz, CH$_3$-21), 1.25, 1.44 [(s, CH$_2$)$_{16}$] 2.14 (t, J=5 Hz, CH$_3$-stearyl), 3.67 (s-COOCH$_3$), 3.91 (d, J=1.5 Hz, CH-7), 3.99 (m, CH-3), 4.4 (m, CH-3), 5.60 (d, J=4.5 Hz, —CH$_2$CONH).

(b) 0.45 g 3β-stearylamido-7α,12α-dihydroxy-5β-cholan-24-oic methylester (FIGS. 1A–6) were dissolved in 20 ml methanol, treated with 2 ml 1N sodium hydroxide and left for 24 h at room temperature. The methanol was then distilled off, 10 ml water were added and the reaction mixture was extracted with ethyl acetate. The water fraction was then acidified with diluted hydrogen chloride, resulting in a white precipitate which was washed with water, to give 0.41 g of the 3β-stearylamido 7α,12α-dihydroxy-5β-cholan-24-oic acid (FIGS. 1A–7). mp 63–65° C.

Method 2

2.5 g 3β-amino-7α,12α-dihydroxy-5β-cholanoic-24-oic acid (prepared according to Kramer et al., J. of Lipid Research 24, 910, 1983) were dissolved in acetonitril and added to a stirred solution of 1.2 g stearic acid and 3.6 g N-hydroxy succinamide in the same solvent. After 8 h the precipitate was filtered, washed with the solvent and evaporated to dryness. The residue was added to a solution of 1.2 g of stearic acid in 10 ml N-methyl morpholine and N,N'-dimethyl formamide (1:3). After being kept at room temperature overnight, the solution was diluted with water, extracted with ethyl acetate, to give 0.6 g of the acid (FIGS. 1A–7), identical to that of Method 1.

Method 3

A solution of 6 g stearoyl chloride was added dropwise to a stirred solution of 1.6 g of the amine (FIGS. 1B–18) in toluene at 0°, and left at the same temperature for 1 h. The resulting solution was heated at 50° for another hour, acidified with 3N-hydrochloride acid, and then filtered. The solid material was washed with water and dried at 45°, to give the acid (FIGS. 1A–7), identical with that described above.

EXAMPLE IV

N-(-Carboxymethyl)-3β-stearylamido-7α,12α-dihydroxy-5β-cholane-24 amide (FIGS. 1B–17)

(a) 0.5 g 3β-stearylamido-7α,12α-dihydroxy-5β-cholanoic acid (FIGS. 1A–7) were dissolved in 25 ml dry 1,4-dioxane and were cooled to −10°. The stirred solution was treated with 0.5 ml triethylamine, then with 0.085 ml chloroethyl formate and stirred at the same temperature for 15 min. The solution was left to reach room temperature, treated with 0.1 ml triethylamine and with 14 g ethyl glycine hydrochloride, and left overnight. The reaction mixture was poured into water, extracted with ethyl acetate and washed with water. The extract was evaporated to dryness and chromatographed on silica gel, using a mixture of ethyl acetate:hexane 60:40, pure ethyl acetate and then ethyl acetate:methanol 9:1, to give 0.27 g of the product (FIGS. 1B–16).

(b) 0.27 g of the above compound were dissolved in 20 ml methanol and treated with 2 ml sodium hydroxide 1N. After 24 h the methanol was evaporated till dryness, dissolved in water and extracted with ethyl acetate. The aqueous fraction was acidified with HCL 1N. The precipitate obtained was washed with water and dried, to give 0.24 g of the dry material (FIGS. 1B–17).

EXAMPLE V

3β-oleylamido-7α12α-dihydroxy-5β-cholan-24-oic acid (FIGS. 1C–20)

(a) 1.6 g 3β-amino-7α12α-dihydroxy-5β-cholan-24-oic methylester (FIGS. 1A–1) were dissolved in 30 ml dry dimethyl formamide and treated with 3 ml triethyl amine under stirring. A solution of 1.38 g oleyl chloride in 10 ml dry DMF was added dropwise, and the resulting solution was left at room temperature overnight. The reaction mixture was poured into water, extracted with ethyl acetate, the organic fraction was purified by washing with diluted hydrochloric acid, sodium bicarbonate and then with water. Evaporation to dryness in vacuum resulted in 3.1 g which were chromatographed over silica gel, using a mixture of ethyl acetate/hexane (4:6 and 10:8) to give 1.8 g of the methyl ester. (FIGS. 1C–19).

(b) A solution of 1.2 g methyl ester in 20 ml methanol was treated at room temperature with a solution of 5 ml sodium hydroxide 1N and kept at room temperature for 48 hours and then evaporated to dryness. The residue was dissolved in 20 ml water and extracted with 25 ml ethyl acetate 3 times. The water extract was acidified with a hydrochloric solution to give a precipitate which was filtered. This residue was chromatographed on silica gel with a mixture of ethyl acetate:hexane:acetic acid (10:4:0.3), to give 0.3 g of 3β-oleylamido-7α12α-dihydroxy-5β-cholan-24-oic acid (FIGS. 1C–20)

EXAMPLE VI

3β,7α-distearylamido-5β-ursodeoxycholan-24-oic acid (FIGS. 1D–26)

(a) 20 g ursodesoxy-cholan-24-oic acid were dissolved in 200 ml abs.methanol, treated with 1 ml conc. sulfuric acid and stirred for 24 hrs. Most of the solvent was distilled off and the residue was poured into water and extracted with methylene chloride. The organic extract was washed with a solution of sodium bicarbonate and of sodium chloride, and evaporated to dryness resulting in 19.5 g of the 3α,7β-dihydroxy-5β-ursodeoxycholan-24-oic acid methyl ester. (FIGS. 1D–21)

$^1$H-NMR (CDCl$_3$) δ, ppm: 0.66 (s, CH$_3$-18), 0.90 (t, J=1 Hz, CH$_3$-23), 0.93 (s, CH$_3$-19), 0.94 (d, J=3 Hz, CH$_3$-21), 3.58 (m, CH-3, CH-7), 3.65 (s-COOCH$_3$).

(b) 4.06 g of the methyl ester (FIGS. 1D–21) were dissolved in 30 ml dry pyridine and cooled to 0° C. The reaction mixture was stirred and treated dropwise for 15 min. with a solution of 1.49 g methane-sulfonyl chloride in 5 ml pyridine. After being left standing for 3 hrs. at the same temperature, the reaction mixture was poured on ice and water, and then extracted with ethyl acetate. The organic phase was washed with hydrochloric acid, sodium bicarbonate and sodium chloride solution, filtered and evaporated in vacuum. The residue consisting of 4 compounds was chromatographed over a silica column using as eluant a mixture of ethyl acetate and hexane. The less polar compound, 5.3 g, was the desired 3α,7β-dimesyl-5β-ursodeoxycholanoic acid 24-oic methyl ester. (FIGS. 1D–22).

$^1$H-NMR (CDCl$_3$) δ, ppm: 0.65 (s, CH$_3$-18), 0.90 (d, J=4 Hz, CH$_3$-23), 0.97 (s, CH$_3$-19), 1.2 (t, J=3 Hz, CH$_3$-21), 2.97 (s, CH$_3$SO$_2$) 1.98 (s, CH$_3$SO$_2$), 3.64 (s, CH$_3$SO$_2$) 4.09 (q, J=12 Hz, H-7), 4.62 (m, H-7)

(c) 5.65 g of the dimesyl derivative were dissolved in 50 ml dry DMF, treated with dry sodium azide and heated to 130° for 2 hrs. The reaction mixture was cooled, poured into ice water and extracted with ethyl acetate. The extract was then washed with a solution of sodium acetate and sodium chloride, filtered and evaporated to dryness, resulting in 4.6 g of the 3β,7α-diazido-5β-ursodeoxycholan-24-oic acid methyl ester (FIGS. 1D–23)

(d) 4.5 g of the diazido compound (FIGS. 1D–23) were dissolved in 120 ml methanol to which 150 mg of 5% palladium on carbon were added and hydrogenated at atmospheric pressure for 4 days. The hydrogenation was repeated with additional 150 mg of 5% palladium on carbon. The hydrogenated mixture was filtered and evaporated in vacuum to give 3 g of the 3β,7α-diamino-5β-ursodeoxycholan-24-oic acid methyl ester (FIGS. 1D–24).

$^1$H-NMR (CDCl$_3$) δ, ppm: 0.65 (s, CH$_3$-18), 0.92 (d, J=4 Hz, CH$_3$-23), 0.96 (s, CH$_3$-19), 1.2 (t, J=3 Hz, CH$_3$-21), 3.68 (s, COOCH$_3$), 3.72, 3.95 (m, 2H-7,3)

(e) 1.47 g of the 3β,7α-diamino-5β-ursodeoxycholan-24-oic acid methyl ester (FIGS. 1D–24) were dissolved in 50 ml of a dry 1:1 mixture of DMSO and DMF, treated with 2 ml triethylamine and 30 mg dimethylamino pyridine and 5.1 g stearic anhydride. The reaction mixture was heated to 50°, stirred for 18 hrs, poured into ice-water and extracted 3 times with ethyl acetate. The organic phase was washed with hydrochloric acid, sodium bicarbonate and sodium chloride solution. After evaporating of the organic solvent 2.05 g of an oily residue were obtained. Separation on silica gel using ethyl acetate:hexane as an eluant (1:4) resulted in a number of fractions, one of which, 80 mg, was the desired 3β,7α-distearyl-amido-5β-ursodeoxycholanoic acid-24-methylester (FIGS. 1D–25), according to its MS and $^1$H-NMR MS FAB: MH+ 937 (MW) 936)

$^1$H-NMR (CDCl$_3$) δ, ppm: 0.66 (s, CH$_3$-18), 0.86 (d, J=4 Hz, CH$_3$-23), 0.96 (s, CH$_3$-19), 1.2 (t, J=3 Hz, CH$_3$-21), 1.26[s, (CH$_2$)$_{16}$], 3.64 (s, COOCH$_3$), 3.05 (d J=7.0 Hz, H-7) 5.75 (m, H-3)

(f) 78 mg of the methylester (FIGS. 1D–25) were dissolved in 20 ml methanol, treated with 2 ml sodium hydroxide 1N and left for 48 hrs at room temperature. The methanol was evaporated in vacuum, the residue was dissolved in 25 ml water, filtered and then acidified with diluted hydrochloric acid to give a precipitate which consisted of 3β,7α-distearylamido-5β-ursodeoxycholan-24-oic acid (FIGS. 1D–26).

EXAMPLE VII

Materials and Methods

Cholesterol (Sigma, St. Louis, Mo.) was twice recrystallized from hot ethanol; Na-taurocholate (Na-TC; Sigma, St. Louis, Mo.) was twice recrystallized from ethanol and ether (J. L Pope, J. Lipid Res. 8, (1967) 146–147); egg yolk lecithin (EYL) (Avanti Polar Lipids, Alabaster, Ala.) was used without further purification. All lipids used in this study were pure by TLC standard.

1. Preparation of Biles

A. Model Bile

EYL, cholesterol and Na-TC mixtures were dissolved in CHCl$_3$/CH$_3$OH (2:1 v/v), dried under N$_2$ at room temperature, lyophilized overnight and kept at −20° C. under argon until used. Model bile solutions were prepared by suspending the dried lipids in 150 mM NaCl, 1.5 mM disodium EDTA, 50 mM Tris-HCl pH 8.0 and incubating the suspension at 55° C. for 1 hour. The solubilized model biles were incubated, in sealed vials under argon, at 37° C. for the duration of the experiment. Aliquots from the models were examined daily.

All models were prepared in triplicate and were kept at the same conditions throughout the experimental period.

The composition of the model bile was:

cholesterol 15 mM, EYL 30 mM, Na-TC 150 mM.

The other investigated model bile solutions were prepared by adding or substituting (10–20%) of the EYL or Na-TC by the synthetic bile acid conjugate.

B. Native human gallbladder bile

Native human gallbladder bile was obtained from cholesterol gallstone patients at cholecystectomy. Pooled bile from several patients was cholesterol enriched by incuvation with dried cholesterol or by mixing with a concentrated model bile prior to use in experiments in order to facilitate crystallization.

2. Evaluation of Cholesterol Crystal Formation and Growth 2.1 Crystal Observation Time (COT) Assay COT (also called "Nucleation time") was determined as described by Holan et. al. in Gastroenterology 77, (1979) 611–617. Aliquots from each model bile were examined daily by polarized light microscopy. COT was defined as the initial time of detection of at least three cholesterol monohydrate crystals per microscopic field at 100 fold magnification.

2.2 Crystal Growth Rate (CGR) Assay

Crystal growth was monitored spectrophotometrically using a microplate reader (SPECTRA-STL, Austria) (G. J. Somjen, et. al. J. Lipid Res. 38, (1977) 1048–1052). Aliquots (50 $\mu$l) of lipid solutions were mixed and shaken vigorously with equivalent volumes of Na-taurodeoxycholate (100 mM), in microplate wells. After 60 minutes at room temperature, the microplates were shaken again and the absorbance, at 405 nm, in each well was measured. Each model was prepared in triplicate and sampled in duplicate for measurement.

The data were collected and analyzed by an IBM compatible personal computer, and the optical density (OD), averaged for triplicate preparations, was calculated. A graph describing the averaged OD changes for each solution was plotted. The slope in the steepest region of the curve was determined by a linear regression fit to at least three measurements and defined as the CGR. CGR and OD differences between day 0 and day 14 were calculated for each model.

2.3 Measurement of Crystal Mass

Chemical analyses of cholesterol were performed on each sample on the last day of the experiment (day 14), as previously described (G. J. Somjen see above). The samples were collected from the micro wells, centrifuged in an Airfuge (Beckman) at 70,000 rpm for 5 min. Separate determinations were performed on the total sample (before centrifugation) as well as on the supernatant solution. The amount of cholesterol in the precipitated pellets was calculated by subtracting the amounts in the supernatant solutions from the total. The crystalline character of the pellet was confirmed by polarized light microscopy. The crystal mass was also measured spectrophotometrically as the OD difference between day 0 and day 14 of the incubation.

3. Data Analysis

Each lipid dispersion was prepared in triplicate and duplicate aliquots were measured from all samples. Mean values of OD and standard errors were calculated. Crystals growth rates were calculated from linear regression analysis of the crystal growth curves as explained above. Comparisons between the different model solutions were performed by one way analysis of variance.

EXAMPLE VIII

The model bile solution had the following composition:

Cholesterol 15 mM, EYL 30 ml, NaTC 150 mL. It was prepared as described in Example VII. In the test solutions 20 mole percent of NaTC were replaced by an equimolar amount of each specific fatty acid/bile acid conjugate tested. The results obtained with the conjugates of saturated fatty acids of chain length $C_{18}$ and $C_{20}$, respectively, conjugated with cholic acid at position $C_3$ are shown in FIGS. 2 and 3.

FIG. 2 shows the effect of these conjugates on the cholesterol crystal mass following 14 days of incubation of the control and test solutions. All the above conjugates reduced the final crystal mass in comparison with the control solution. The $C_{18}$ conjugate reduced it to 14% of the control; the $C_{20}$ conjugate reduced it to 38%.

A conjugate of $C_{22}$ tested in a different experiment showed a similar activity to that of $C_{20}$.

Figure 3:
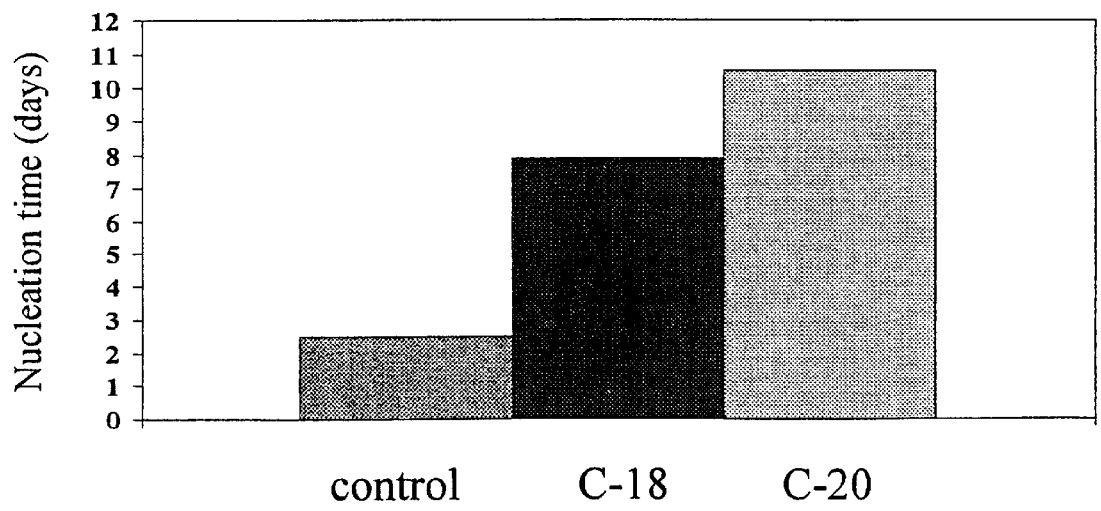
FIG. 3 shows the nucleation time. Model bile solution. Effects of the compounds used in FIG. 2.

FIG. 3 shows the nucleation time (crystal observation time) of the various test solutions as compared to the control solution. Replacement of 20% of the bile salt (NaTC) by the specific conjugates resulted in a prolongation of the nucleation time with $C_{18}$ and $C_{20}$ conjugates. The $C_{20}$ conjugate prolonged the nucleation time by more than 360%.

EXAMPLE IX

Figure 4:
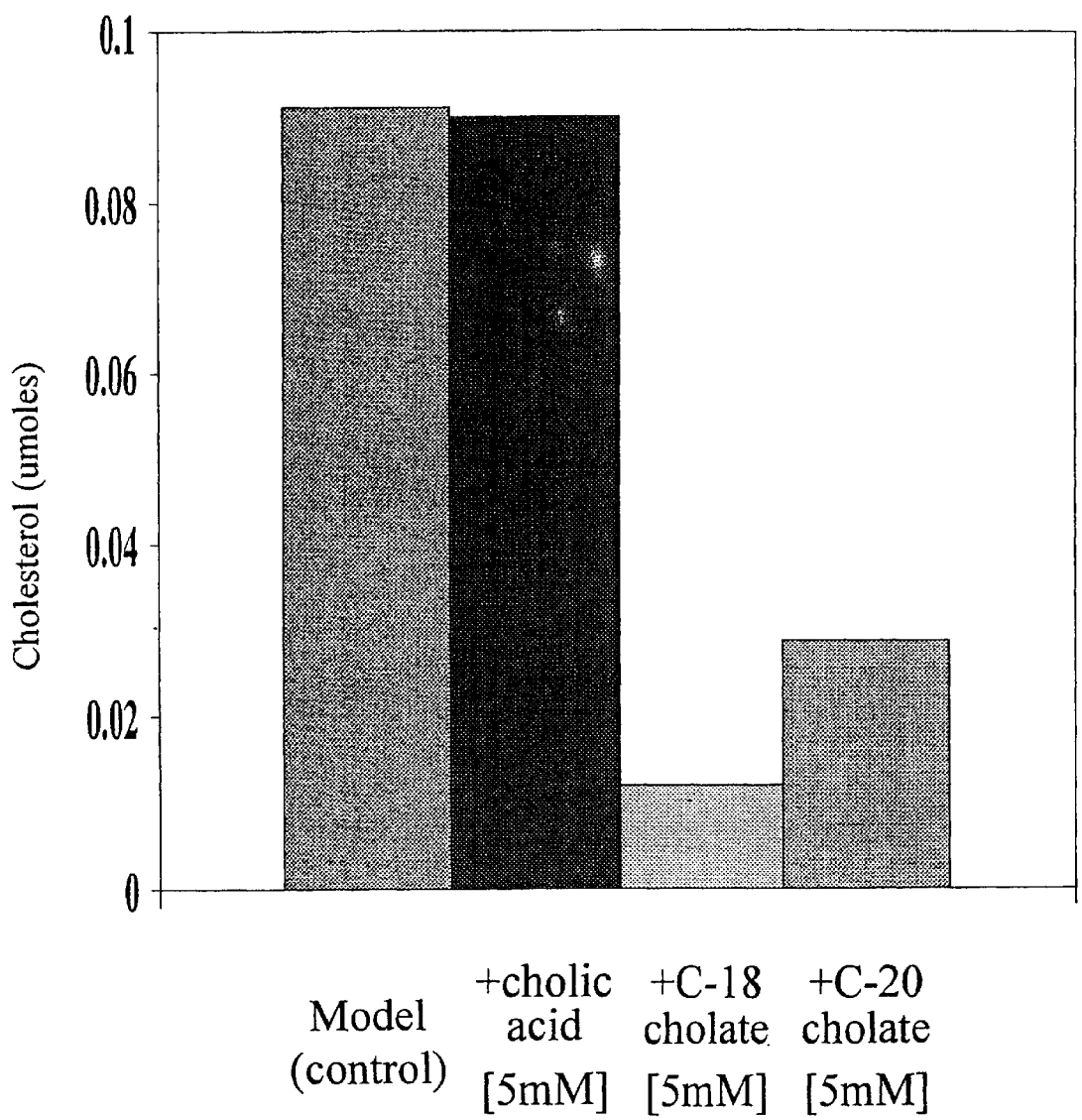
FIG. 4 shows the cholesterol crystal mass of enriched human bile after 22 days of incubation. Effects of 5 mM stearoyl (C-18) cholate and arachidyl (C-20) cholate added to the bile in comparison with the control bile and bile with added 5 mM cholic acid.

Pooled human gallbladder bile obtained at operations was enriched with a concentrated lipid solution to enhance cholesterol crystallization. The final concentration in bile of the added lipids was NaTC 60 mM, EYL 18.4 mM and cholesterol 9.2 mM. The enriched bile was ultracentrifuged at 50,000 rpm for 1 hour to remove cholesterol crystals and was then distributed into 4 vials. The first vial contained only enriched bile (control). To the other 3 vials the following solutions were added (at 5 mM): cholic acid, C-18 (stearoyl) cholate and C-20 (arachidyl) cholate. Following 22 days of incubation at 37° C. all biles were centrifuged in an airfuge at 70,000 rpm for 5 minutes. The sediment was removed and its cholesterol content measured chemically. The results are shown in FIG. 4, as $\mu$ moles of cholesterol in the sedimented crystal mass. It is obvious that both bile salt/fatty acid conjugates very markedly reduced cholesterol crystallization in comparison to the control bile with or without cholic acid.

EXAMPLE X

A model bile solution was prepared as described in example VII, with the same lipid composition, and served as a control. In all other samples 20 mole % of the NaTC were replaced by equimolar amounts of: cholic acid, $C_{18}$ cholate and $C_{20}$ cholate (all these saturated fatty acids were conjugated at position $C_3$ of the cholate) and di-stearoyl ursodeoxycholate (with the stearic acid radicals conjugated in equal proportions at positions $C_3$ and $C_7$ of the bile acid).

Figure 5:
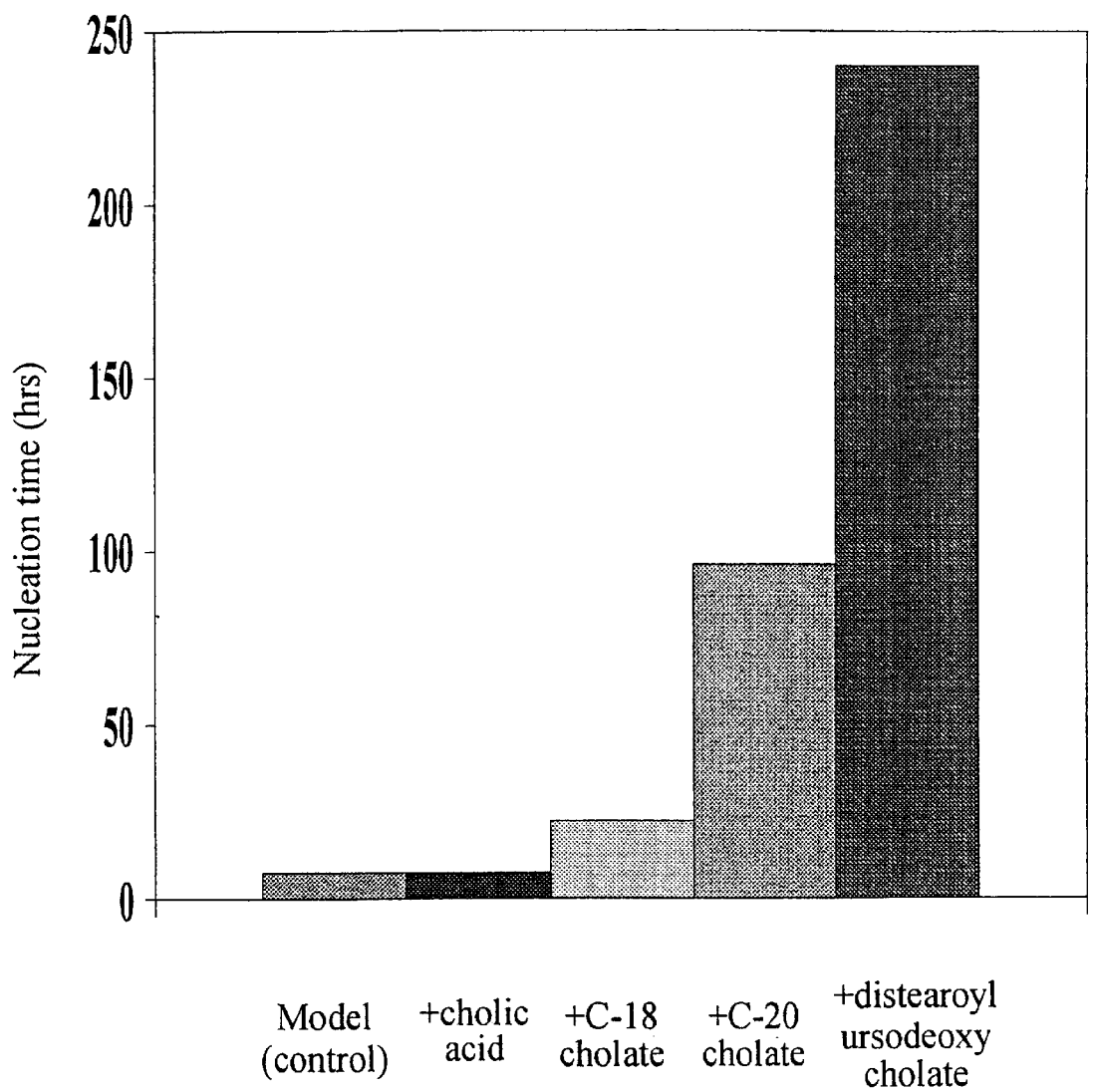
FIG. 5 shows the nucleation time, model biles. Effects of replacement of 20 mole % of NaTC with equimolar amounts of several BAFAC's comprising stearoyl (C-18) cholate, arachidyl (C-20) cholate and di-stearoyl ursodeoxycholate in comparison with the model bile with and without replacement of 20% of NaTC with cholic acid.

All samples were incubated at 37° C. in the same manner as described in example VII and the nucleation time was determined by periodic light microscopic observations. The results are shown in FIG. 5. The results proved that: 1) All conjugates (BAFAC) tested retarded cholesterol crystallization as compared to the control model bile and to equimolar amounts of cholic acid. 2) That BAFAC with longer fatty acid chains were more effective than those with shorter chains. 3) That the conjugate with 2 fatty acids (distearoyl ursodeoxycholate) was particularly effective.

EXAMPLE XI

Absorption and Transport of Stearoyl-Cholate (C-18 Cholate)

Female hamsters weighing 80–100 gms were given a single dose of 30 mg of C-18 cholate by intragastric administration. Single animals were sacrificed at 1, 2, and 3 hours after administration. Heart blood, portal blood and gallbladder bile were sampled. Two groups of animals (A and B) were studied in parallel. Stearoyl cholate levels were measured with a HPLC instrument (Kontron Switzerland) using a UV detector at 206 nm.

The results are shown in FIGS. 6A and 6B.

In group A: Heart blood levels after 1, 2 and 3 hours were 99,7,2 $\mu$M, while portal blood levels were 68,99 and 133 $\mu$M, respectively. C-18 cholate levels in gallbladder bile were 540 and 270 $\mu$M at 2 and 3 hours, respectively. Results in group B were similar.

The data show: 1) That C-18 (stearoyl) cholate is absorbed from the intestine. 2) That it is transported both in the systemic circulation (via the lymph) and in the portal vein 3) That it is actively secreted into the bile and concentrated in it.

EXAMPLE XII

A model bile solution was prepared in the same manner as described in Example VII. It had the same lipid composition and served as control.

In the test solutions cholic acid, stearoyl (C-18:0) cholate and oleoyl (C-18:1) cholate were added in 20 mM concentrations. All samples were incubated at 37° C. for 100 hrs The difference in the optical density between 100 hrs. and 0 hrs (as described in Example VII) was used to measure the total crystal mass at 100 hrs. In comparison with the control solution (100%) the crystal mass with cholic acid was 114%, with stearoyl-cholate 62% and with oleoyl-cholate 55%.

These results prove that BAFAC with a saturated as well as with an unsaturated (oleic) acid both decrease cholesterol crystallization in comparison with the control bile and with equimolar amounts of cholic acid.

What is claimed is:

1. A bile acid or bile salt fatty acid conjugate of one of the formulae

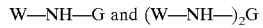

W—NH—G and (W—NH—)$_2$G in which G is a bile acid or bile salt radical which is optionally conjugated in position 24 with a suitable amino acid, and each W is a fatty acid radical having from 18 to 22 carbon atoms.

2. A bile acid or bile salt fatty acid conjugate according to claim 1, wherein the bile acid is a member selected from the group consisting of cholic acid, chenodeoxycholic acid, ursodeoxycholic acid and deoxycholic acid.

3. A bile acid or bile salt fatty acid conjugate according to claim 1, wherein the amino acid in position 24 is a member selected from the group consisting of glycine and taurine.

4. A bile acid or bile salt fatty acid conjugate according to claim 1, wherein the conjugation with the fatty acid radical is at position 3 of the bile acid nucleus.

5. A bile acid or bile salt fatty acid conjugate according to claim 1, wherein the conjugation with the fatty acid radical(s) is at a position selected from the 6, 7, 12 and 24 positions of the bile acid nucleus.

6. A bile acid or bile salt fatty acid conjugate according to claim 1, wherein the conjugation between the fatty acid radical(s) and the bile acid is in the $\alpha$ or the $\beta$ configuration.

7. A bile acid or bile salt fatty acid conjugate according to claim 1, wherein the fatty acid is a member selected from the group consisting of behenylic acid, arachidylic acid and stearic acid.

8. A bile acid conjugate according to claim 1, which is 3$\beta$-behenylamido-7$\alpha$,12$\alpha$-dihydroxy-5-cholan-24-oic acid.

9. A bile acid conjugate according to claim 1, which is 3$\beta$-arachidylamido-7$\alpha$,12$\alpha$-dihydroxy-5-cholan-24-oic acid.

10. A bile acid conjugate according to claim 1, which is 3$\beta$-stearylamido-7$\alpha$,12$\alpha$-dihydroxy-5-cholan-24-oic acid.

11. A bile salt fatty acid conjugate according to claim 1, which is N-(carboxymethyl)-3$\beta$-stearylamido-7$\alpha$,12$\alpha$-dihydroxy-5$\beta$-cholan-24-amide.

12. A bile acid or bile salt fatty conjugate according to claim 1, wherein there are two W's which are conjugated at positions 3 and 7 of the bile acid nucleus.

13. A pharmaceutical composition which enables dissolution of cholesterol gallstones in bile and for preventing formation thereof and enabling prevention and/or reduction of arterisclerosis, which composition comprises, as active ingredient, a bile acid or bile salt fatty acid conjugate according to claim 1, in combination with a carrier, a solvent, an emulgator, an enhancer of absorption, or an inhibitor of cholesterol synthesis or secretion into the bile.

14. A pharmaceutical composition according to claim 13, which is in tablet, capsule, solution or emulsion form.

15. A pharmaceutical composition according to claim 13, comprising from 0.1 to 1.5 g of the active ingredient.

16. A method which comprises dissolving cholesterol gallstones in bile or for preventing formation of such gallstones which comprises administering an effective amount of a bile acid or bile salt fatty acid conjugate according to claim 1 to a subject in need of such therapy.

17. A method which comprises dissolving cholesterol gallstones in bile or for preventing formation of such gallstones which comprises administering an effective amount of a pharmaceutical composition according to claim 13 to a subject in need of such therapy.

18. A method for preventing and/or reducing arterisclerosis which comprises administering an effective amount of a bile acid or bile salt fatty acid conjugate according to claim 1 to a subject in need of such therapy.

19. A method for preventing and/or reducing arterisclerosis which comprises administering an effective amount of a pharmaceutical composition according to claim 13 to a subject in need of such therapy.

* * * * *

UNITED STATES PATENT AND TRADEMARK OFFICE
Certificate

Patent No. 6,395,722 B1            Patented: May 28, 2002

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Tuvia Gilat, Tel Aviv, Israel; and Werner Kramer, Mainz-Laubenheim, Germany.

Signed and Sealed this Twenty-Second Day of July 2003.

JOSE DEES
*Supervisory Patent Examiner*
Art Unit 1616